United States Patent
Strohhoefer et al.

(10) Patent No.: US 10,099,000 B2
(45) Date of Patent: Oct. 16, 2018

(54) DEVICE AND METHOD FOR IDENTIFYING A MALFUNCTION IN AN EXTRACORPOREAL BLOOD CIRCULATION

(71) Applicant: B. BRAUN AVITUM AG, Melsungen (DE)

(72) Inventors: Christof Strohhoefer, Kassel (DE); Jens Schreiber, Kassel (DE); Jennifer Steger, Melsungen (DE)

(73) Assignee: B. BRAUN AVITUM AG, Melsungen (DE)

( * ) Notice: Subject to any disclaimer, the term of this patent is extended or adjusted under 35 U.S.C. 154(b) by 338 days.

(21) Appl. No.: 14/633,663

(22) Filed: Feb. 27, 2015

(65) Prior Publication Data

US 2015/0306301 A1  Oct. 29, 2015

(30) Foreign Application Priority Data

Feb. 28, 2014  (DE) ........................ 10 2014 102 730

(51) Int. Cl.
*A61M 1/36* (2006.01)
*G01L 11/00* (2006.01)
(Continued)

(52) U.S. Cl.
CPC ............ *A61M 1/3656* (2014.02); *A61M 1/14* (2013.01); *A61M 1/34* (2013.01); *A61M 1/3607* (2014.02);
(Continued)

(58) Field of Classification Search
CPC combination set(s) only.
See application file for complete search history.

(56) References Cited

U.S. PATENT DOCUMENTS 6,090,048 A * 7/2000 Hertz ................ A61M 5/16859
600/485
6,595,942 B2  7/2003 Kieinekofort
(Continued)

FOREIGN PATENT DOCUMENTS

CN   204815059 U   12/2015
DE   198 48 235      3/2000
(Continued)

OTHER PUBLICATIONS

European Search Report for EP 15 15 4738 dated Jul. 3, 2015.
(Continued)

*Primary Examiner* — Mamadou Diallo
(74) *Attorney, Agent, or Firm* — RatnerPrestia

(57) ABSTRACT

Methods and systems for identifying a malfunction in the extracorporeal blood circulation of a dialysis machine are disclosed. The malfunction may be identified by detecting at least one state parameter; determining a first evaluation criterion for identifying a malfunction in the extracorporeal blood circulation (FEB); using the first evaluation criterion, making a decision with respect to the presence of a malfunction in the extracorporeal blood circulation, generating a first error signal, and monitoring the detected state parameter; determining at least one further evaluation criterion; using the at least one further evaluation criterion, making a decision with respect to the presence of a malfunction in the extracorporeal blood circulation and generating at least one further error signal; combining the first error signal and the at least one further error signal to result in a combined error signal; and triggering an alarm if the combined error signal exceeds a predetermined limit value.

15 Claims, 4 Drawing Sheets

(51) Int. Cl.
*A61M 1/14* (2006.01)
*A61M 1/34* (2006.01)
*G01F 1/00* (2006.01)
*A61M 39/10* (2006.01)

(52) U.S. Cl.
CPC ........ *A61M 1/3621* (2013.01); *A61M 1/3639* (2013.01); *A61M 1/3653* (2013.01); *G01F 1/00* (2013.01); *G01L 11/00* (2013.01); *A61M 2039/1005* (2013.01); *A61M 2205/13* (2013.01); *A61M 2205/14* (2013.01); *A61M 2205/15* (2013.01); *A61M 2205/17* (2013.01); *A61M 2205/18* (2013.01); *A61M 2205/3344* (2013.01)

(56) References Cited

U.S. PATENT DOCUMENTS

| | | | |
|---|---|---|---|
| 7,648,474 B2 | 1/2010 | Paolini et al. | |
| 2001/0007930 A1 | 7/2001 | Kleinekofort | |
| 2003/0152482 A1* | 8/2003 | O'Mahony | A61M 1/3653 422/44 |
| 2008/0171960 A1* | 7/2008 | Brieske | A61M 1/1698 604/4.01 |
| 2012/0330214 A1* | 12/2012 | Peters | A61M 1/3663 604/6.11 |
| 2014/0166579 A1 | 6/2014 | Gagel et al. | |
| 2014/0277894 A1* | 9/2014 | Doyle | G01C 21/3407 701/23 |
| 2014/0296766 A1* | 10/2014 | Krause | A61M 1/1609 604/6.11 |
| 2015/0196701 A1* | 7/2015 | Ritter | A61M 1/3607 210/646 |
| 2016/0270733 A1* | 9/2016 | Hansson | A61B 5/0215 |
| 2017/0128653 A1* | 5/2017 | Yuds | A61M 1/282 |

FOREIGN PATENT DOCUMENTS

| | | |
|---|---|---|
| DE | 10 2012 024341 | 2/2014 |
| EP | 1 584 339 | 10/2005 |
| EP | 1 815 878 | 8/2007 |
| WO | WO 00/66197 | 11/2000 |

OTHER PUBLICATIONS

Jane A. Hurst, "Venous Needle Dislodgement—A Universal Concern," European Nephrology, 2011, pp. 148-151.
German Search Report for DE 10 2014 102 730.2 dated Dec. 10, 2014.
Chinese Office Action for Chinese Application No. 201510091587.6, dated Apr. 3, 2018 with translation, 24 pages.

* cited by examiner

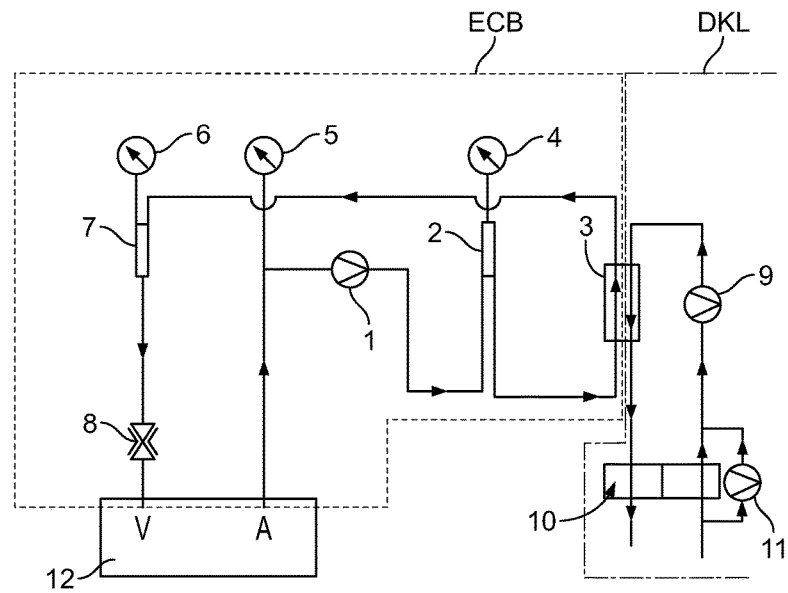
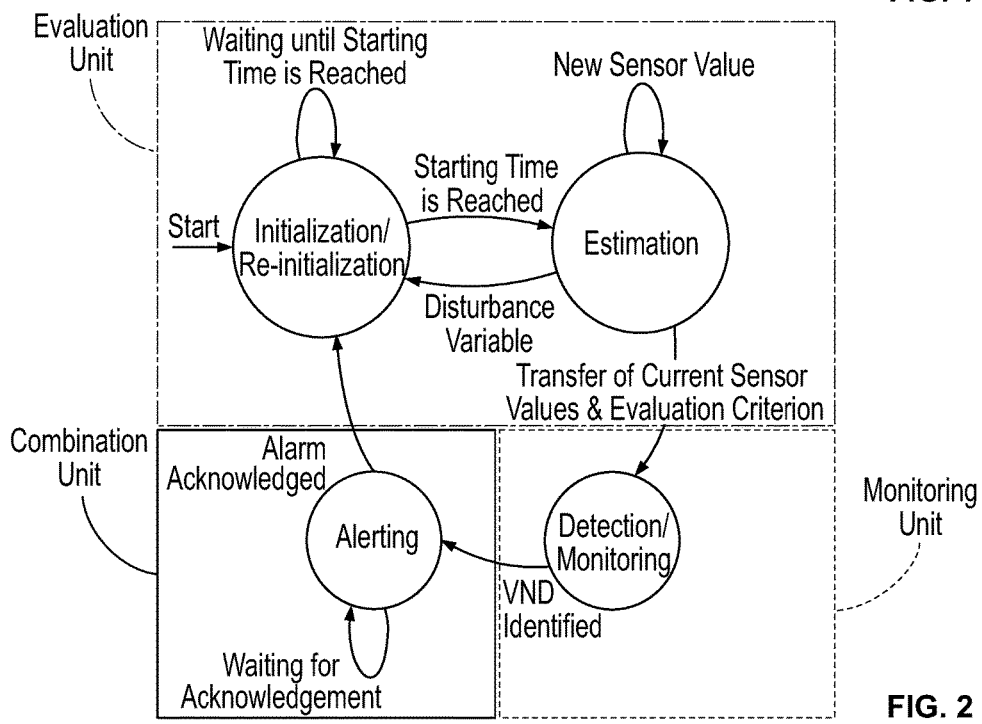
FIG. 1
FIG. 2

DEVICE AND METHOD FOR IDENTIFYING A MALFUNCTION IN AN EXTRACORPOREAL BLOOD CIRCULATION

CROSS REFERENCE TO RELATED APPLICATIONS

This application claims priority to German application DE 10 2014 102 730.2 filed Feb. 28, 2014, the contents of such application being incorporated by reference herein.

FIELD OF THE INVENTION

The invention relates to a device and a method for identifying a malfunction in the extracorporeal blood circulation of a device for extracorporeal blood treatment. An example of such a malfunction is a venous needle disconnection (VND).

BACKGROUND

For an extracorporeal blood treatment with a device such as a dialysis machine, blood of a patient is conveyed through an extracorporeal blood circulation for instance in the course of a hemodialysis, hemofiltration or hemodiafiltration. In order to gain access to the intracorporeal blood vessel system of the patient, arteriovenous fistulas, shunts or also vessel implants are used as a rule. The connection between the extracorporeal blood circulation and the patient is usually effected with catheters or cannulas or needles, e.g. dialysis cannulas or needles, which serve for puncturing a fistula, shunt or vessel implant, for example.

In the context of such a blood treatment, malfunctions may occur in the extracorporeal blood circulation, which are shortly termed as FEB. One example of an FEB is a needle disconnection. In such a situation, the access to the blood circulation of the patient is defective, for instance if a needle or cannula gets out of place and the extracorporeal circulation is not properly connected to the intracorporeal blood circulation or patient's blood circulation any more. This may be problematic in particular in the event of a disconnection of a venous access to the patient's blood circulation. If such incident is not identified in due time, blood is still taken from the patient via an arterial access, but is not conveyed back to the patient (or only in an unsufficient amount) after the extracorporeal blood treatment. With the usual blood flow rates of approximately 300 to 400 ml/min, a life-threatening situation may arise within few minutes.

The identification of malfunctions in the extracorporeal blood circulation, in particular the recognition of a venous needle disconnection, is a severe problem in medical treatments using an extracorporeal blood circulation such as the hemodialysis. In the USA alone, approximately one hundred people die each year from the consequences of a venous needle disconnection (Hurst, Jane, "Venous Needle dislodgement—A Universal Concern." European Nephrology).

DESCRIPTION OF THE RELATED ART

Known methods and systems for identifying a malfunction in the extracorporeal blood circulation, in particular for detecting it prior to the development of serious consequences for the patient, have shortcomings in a disadvantageous way. Moreover, known methods and systems are prone to false alarms in most cases. Frequent false alarms are just as critical as unrealized FEBs, as they result in the staff becoming emotionally blunted.

There are known methods of identifying a malfunction in the extracorporeal blood circulation (FEB), which are based on an analysis of the venous (and/or arterial) pressure. EP 1 584 339 B1, for instance, discloses a method of identifying a needle disconnection on the basis of a measurement of arterial and venous pressures with involving summation and subtraction processes.

U.S. Pat. No. 7,648,474 B2 discloses a device monitoring arterial and venous pressure values for determining a needle disconnection.

EP 1 815 878 B1 discloses a blood cleaning device comprising means for measuring the venous blood pressure of a patient and means for monitoring the venous blood pressure, an alarm being activated by comparing a predetermined alarm threshold value with a measured pressure or with a pressure whose measurement is predicted, the means for monitoring the venous blood pressure updating the predetermined alarm threshold value with a predetermined time period.

A disadvantage of known methods is that they cover only a limited range of pressure characteristics of malfunctions in the extracorporeal blood circulation. This is because malfunctions occurring in the extracorporeal blood circulation usually have no unique characteristic, but a broad band of possible characteristics. A single method or monitoring system based on the analysis of sensor values is not able to fully cover said band of possible characteristics and at the same time exclude other possible causes (apart from an FEB) for sensor fluctuations.

SUMMARY OF THE INVENTION

Starting from the prior art described above, the invention relates to an object to provide an improved method as well as an improved system for identifying a malfunction in the extracorporeal blood circulation and for monitoring the integrity of the extracorporeal blood circulation in an extracorporeal blood treatment. A plurality of malfunctions in the extracorporeal blood circulation is supposed to be able to be detected with high safety and reliability. Moreover, false alarms are supposed to be avoided. The monitoring shall be carried out preferably on the basis of sensor values, and life-threatening situations e.g. due to the blood loss of a patient shall be able to be reliably avoided.

This object is achieved according to aspects of the invention by a malfunction identification method according to method claims herein and a malfunction identification system according to system claims herein. Advantageous configurations of the invention are also subject matter of the claims. With regard to the method, this object is achieved by a method for identifying a malfunction in an extracorporeal blood circulation of a device for an extracorporeal blood treatment (in the following "blood treatment machine"), e.g. a dialysis machine, wherein at least one state parameter is detected, a first evaluation criterion for identifying a malfunction in the extracorporeal blood circulation (FEB) is determined and, using the first evaluation criterion, a decision is made with respect to the presence of a malfunction in the extracorporeal blood circulation and a first error signal is generated as well as the detected state parameter is monitored, wherein at least one further state parameter evaluation criterion is determined and, using the at least one further evaluation criterion, a decision is made with respect to the presence of a malfunction in the extracorporeal blood circulation and a further error signal is generated, the first error signal and the at least one further error signal are combined to result in a combined error signal, and an alarm is preferably triggered if the combined error signal exceeds a predetermined limit value (in the positive as in the negative sense).

With regard to the device, the mentioned object is achieved by a system for identifying a malfunction in the extracorporeal blood circulation of an extracorporeal blood treatment machine, for instance of a dialysis machine, comprising at least one sensor for detecting at least one state parameter, an evaluation unit for determining a first evaluation criterion for identifying a malfunction in the extracorporeal blood circulation (FEB), a monitoring unit for making a decision with respect to the presence of a malfunction in the extracorporeal blood circulation and for generating a first error signal as well as for monitoring the detected state parameter, in each case by making use of the first evaluation criterion, the system comprising at least one further evaluation unit in order to determine at least one further evaluation criterion, the system comprising at least one further monitoring unit for the purpose of making a decision with respect to the presence of a malfunction in the extracorporeal blood circulation and generating at least one further error signal, in each case by use of the at least one further evaluation criterion, and the system comprising a combination unit for combining the first error signal and the at least one further error signal to a combined error signal. The system of the invention may be suitable and intended for carrying out the method according to aspects of the invention, in particular for performing a method according to any of the attached claims.

The extracorporeal blood treatment machine, preferably a dialysis machine, may serve for carrying out chronic blood cleaning therapies in the broadest sense, such as a hemodialysis, hemofiltration or hemodiafiltration. The invention detects/ascertains any malfunctions in the extracorporeal blood circulation, which are briefly termed as FEB. Such an FEB, for example, may be present in the form of a clogging or closure or constriction of the extracorporeal blood circulation, or exist in the form of a leakage. One example for an FEB is a needle disconnection, in particular a venous needle disconnection (briefly VND).

The term "state parameter" is to be understood as a general term and may include in particular a hemodynamic state parameter. The (at least one) state parameter may be a parameter of a patient, a parameter of the extracorporeal blood circulation or a parameter of other units of the dialysis machine. It may be detected prior to and/or during and/or after a treatment in continuous as well as in discontinuous manner. It is preferred that the (at least one) state parameter is detected with a suitable sensor or a suitable sensor unit. In the context of the invention, a single or several state parameters can be detected. Examples of the at least one state parameter are the venous blood pressure and/or the arterial blood pressure, or the blood flow rate or any such parameters related to fluid mechanics. Further state parameters could also be the following: hematocrit, density, chemical composition of the blood plasma, concentration of individual substances in the blood, each individually or in combination as a concentration ratio.

According to aspects of the invention, the determination of evaluation criteria for one or several detected state parameters can be carried out preferably with one evaluation unit or several evaluation units. The monitoring of the detected state parameters using the first evaluation criterion or the further evaluation criteria may be performed according to aspects of the invention in particular by one monitoring unit or several monitoring units. The combination of the error signals may occur according to aspects of the invention in particular with weighted or unweighted case analyses, fuzzy models, neuronal networks, SVRs or physical or mathematical models, which depend for instance on the temperature or other physical variables.

In other words, three different units are employed according to aspects of the invention for monitoring the dialysis machine, i.e. on the one hand one evaluation unit or several evaluation units determining an evaluation criterion for identifying an FEB, secondly a monitoring unit or several monitoring units determining an FEB from the determined evaluation criteria of the evaluation unit, and in the third place one combination unit or several combination units combining, according to aspects of the invention, several monitoring units and hence indirectly combining evaluation units as well. One, several or all of the mentioned units may each comprise a memory unit, an arithmetic unit, an energy supply means and a data line.

Evaluation criteria are determined in the evaluation units. According to aspects of the invention, the first evaluation criterion and the at least one further evaluation criterion may be identical or different. Suitable evaluation criteria may be determined e.g. by a polynomial regression and an exponentially weighted, moving average.

The monitoring unit generates an error signal which is delivered to the combination unit. In particular, a monitoring unit is capable of generating an error signal which is set to a specific first value in the event of an identification of a malfunction in the extracorporeal blood circulation and is set to another, second value in case no FEB is detected.

The combination unit is used for combining any number of monitoring units—and hence also the error signals generated by them—to a combined error signal. This combination has a crucial advantage. The presence of an FEB is derived not only on the basis of an evaluated error signal, as is known from prior art, but the combination unit processes a plurality of error signals which have been evaluated preferably in different ways. The strengths and weaknesses of the respective evaluation units and the evaluations performed therein are known or can be ascertained, and in this way it is possible to improve the quality of identifying and displaying the malfunction and avoid false alarms by a targeted selection or processing of the error signals delivered from the monitoring units to the combination unit. The device according to aspects of the invention and the method according to aspects of the invention allow in particular to perceive a venous needle disconnection at an early stadium. This ensures a high safety for the patient during a treatment such as a dialysis treatment and a high functional reliability as well.

An error signal generated by a monitoring unit may be of binary nature, e.g. 0 for no. FEB or for connection and 1 for FEB or disconnection. As an alternative, an error signal may be present in non-binary form, e.g. in the form of values in a range from 0 to 1. Also a combination of said variants is within the scope of the invention; it is possible, for example, that an error signal of a monitoring unit is present in binary form and an error signal of another monitoring unit is present in non-binary form. The use of non-binary error signals has the advantage that—in the course of a decision whether an FEB exists or not—it can be taken into consideration how far a fixed limit value for the presence of an FEB has been exceeded in positive or negative direction.

Up to now, there is no method which allows to combine various identification methods for identifying malfunctions in the extracorporeal blood circulation, such as a VND, for example. The present invention allows a combination of various evaluation units for identifying an FEB. Furthermore, a targeted percentage for identifying malfunctions can be allocated to individual evaluation methods, which means that the evaluation methods can be weighted differently. In addition, individual evaluation methods can be started at defined, different points in time. This enables a detection system to exploit the specific strengths of each included evaluation unit, i.e. of each evaluation method which is employed, and to compensate for its weaknesses by the strengths of another evaluation unit.

Further developments of the aspects of the invention are defined in the dependent claims. By way of example, the first error signal and/or the at least one further error signal may be subjected to a weighting process. In particular all error signals can be weighted. In the course of such a weighting process, one error signal or several error signals is/are multiplied with a factor (the weighting). The factor size used in this process, i.e. the weighting of the error signals, can be selected as desired. Due to the weighting, it is possible to provide for instance an error signal—which is known to be possibly prone to errors in certain periods of time or under certain circumstances—with a smaller weighting, whereas another error signal which is less prone to errors can be provided with a higher weighting. A limit value of the error signals, in particular of the weighted error signals, which indicates an FEB when it is reached or exceeded, may allow in dependence of the weightings or the combined error signal to draw conclusions with respect to the kind of the FEB.

To give an example, a factor of 0.5 as the weighting can be chosen for each error signal in a method of the aspects of the invention in which three binary error signals are generated. A limit value fixed for the presence of an FEB can be set to a value of 1. In this exemplary case, an FEB alarm is triggered as soon as two error signals output by the monitoring units have detected an FEB. With such adjustments, approximately 95% of all FEBs have been recognized in tests and the number of false alarms could be reduced by approximately 8% as compared to the existing systems.

According to one embodiment of the invention, the first error signal and the at least one further error signal can be combined by summing up the error signals, in particular the weighted error signals. The error signals can be added up in particular in an arithmetic unit. If this sum exceeds a limit value, leaves a specific range and/or lies in a specific range, one can assume the presence of an FEB; on this occasion, it is preferred to trigger an alert. The error signals of the monitoring units may also be combined with other mathematical methods and models. In doing so, a model can be adapted to the individual monitoring units. Possible other combination variants belong to the field of machine learning, such as weighted or unweighted case analyses, fuzzy models, neuronal networks, SVRs or physical or mathematical models which depend e.g. on the temperature or any other physical variables.

According to a further embodiment of the invention, an initialization can be carried out. In doing so, an initialization can be performed for at least one detected state parameter by allocating an initial value to the state parameter and determining the evaluation criterion by use of the initial value as well as using state parameters detected after the initialization.

According to another embodiment, the monitoring of a detected state parameter and the detection of a malfunction with the first evaluation criterion may run or begin with a temporal offset relative to the monitoring of a detected state parameter and the detection of a malfunction with the at least one further evaluation criterion. Such a temporal offset may occur in particular after a system startup and/or an initialization and/or a re-initialization.

According to one embodiment, at least one disturbance variable may be detected, in particular one of the type which has the same or a similar impact on the sensor values as an FEB. Said disturbance variable(s) can be taken into consideration for a decision with respect to the presence of a malfunction. Disturbance variables can be detected especially in continuous manner and/or with any desired scanning rate. Examples for a disturbance variable are especially an ultra filtration rate, a dialysis fluid flow rate, a blood flow rate, a level control or a preceding alarm. Having detected a disturbance variable, especially a re-initialization can be carried out with advantage. With such a detection of disturbance variables, it is possible in an advantageous manner to avoid false alarms. A successful reduction of false alarms allows with special advantage to reduce or prevent the emotional blunting of nursing staff with respect to alerting situations.

The system according to aspects of the invention may be in particular a part of a blood treatment device, for instance of a dialysis device. Especially, it may comprise a display device and/or an alarm device for generating an indication or an alarm in the event of the output of a combined error signal.

BRIEF DESCRIPTION OF THE DRAWINGS

The invention is best understood from the following detailed description when read in connection with the accompanying drawings. Included in the drawings are the following figures:

FIG. 1 shows a blood circulation of a dialysis machine during a hemodialysis,

FIG. 2 is a schematic illustration of state machines for an evaluation unit and monitoring unit.

DETAILED DESCRIPTION OF THE PREFERRED EMBODIMENTS

Figure 3:
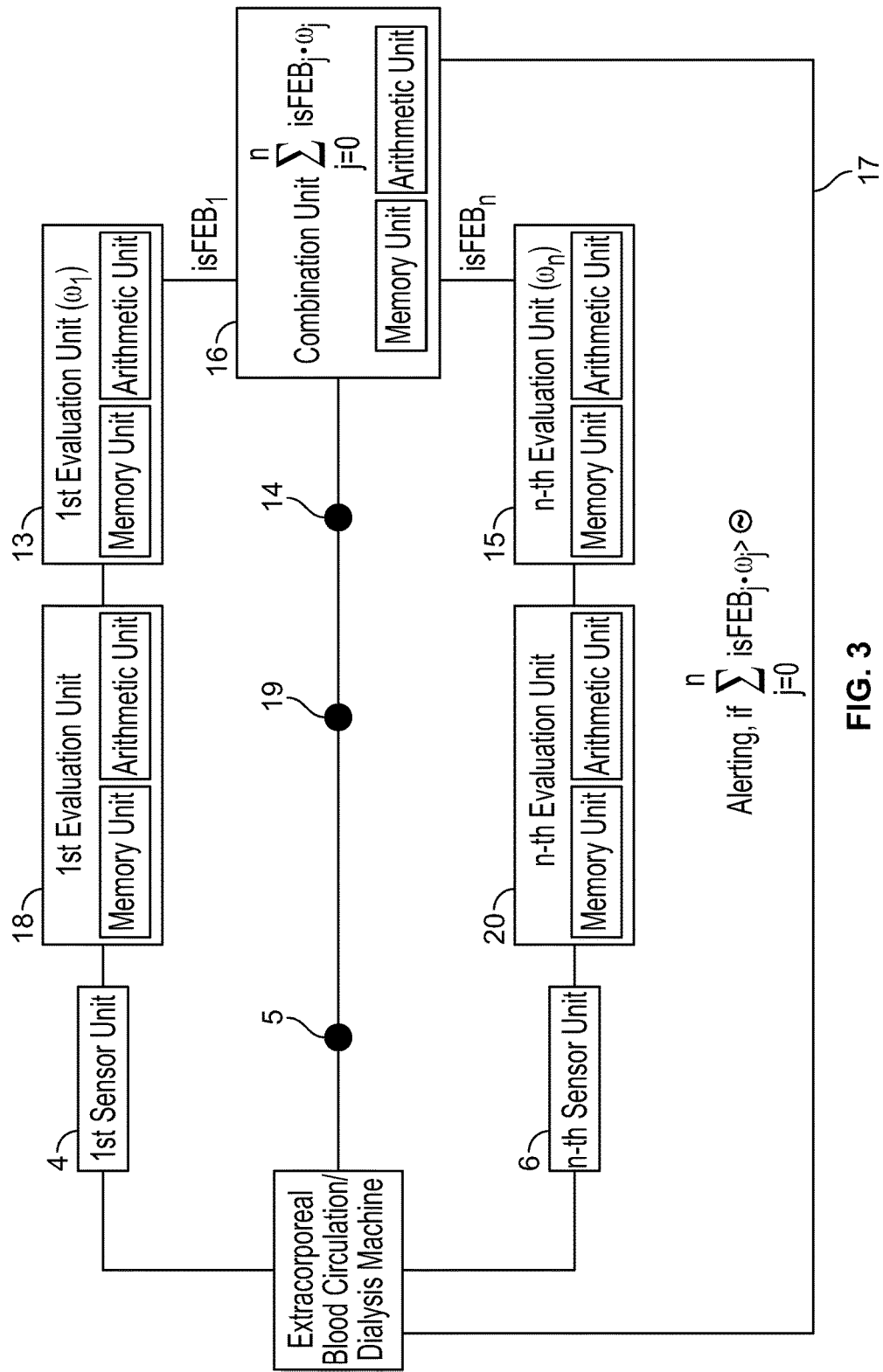
FIG. 3 is a schematic illustration of a first embodiment of a system according to aspects of the invention.

The description of the invention on the basis of the exemplary embodiments of the system according to aspects of the invention and the method according to aspects of the invention is made with reference to so-called venous needle disconnections or dislodgements (VND, "Venous Needle Dislodgement"). This reference to VND is not limiting and the invention and the described exemplary embodiments may serve for detecting any malfunctions in the extracorporeal blood circulation of a blood treatment device.

Due to movements of the patient or because of an inadequate fastening of a needle or cannula on a patient or due to an insufficient attachment of a blood conduit of an extracorporeal blood circulation to a needle/cannula as the connection between the patient's bloodstream and the extracorporeal blood circulation of a dialysis machine, the needle may get unloosed completely or in part, i.e. a disconnection may occur. This is problematic in particular with a venous needle, as the blood which is correspondingly pressurized is returned back to the patient via said needle. This may additionally increase the risk of a disconnection.

FIG. 1 schematically shows liquid systems of a dialysis machine for a hemodialysis. Instead of or in addition to a hemodialysis, a pure hemofiltration or a hemodiafiltration may be implemented. The dialysis machine is equipped with a system according to aspects of the invention for identifying a malfunction in the extracorporeal blood circulation and is adapted and suited for carrying out a method according to aspects of the invention. The explained exemplary embodiment relates to a venous needle disconnection as one kind of a malfunction in the extracorporeal blood circulation.

In general, FIG. 1 illustrates an extracorporeal system in the form of an extracorporeal blood circulation (ECB) as well as a dialysis fluid system in the form of a dialysis fluid circulation (DKL).

The extracorporeal blood circulation (ECB) connects the dialysis patient 12 to the dialysis machine. During a therapy, blood is taken from the patient 12 via an arterial cannula A and is conveyed, with an arterial blood pump 1 disposed in an arterial blood conduit, to a dialyzer 3 via an arterial air trap 2. The actual treatment of the blood, here a cleaning process, is performed in the dialyzer 3. The blood flows from the dialyzer 3 via a venous air trap 7 in a venous blood conduit and via a venous cannula V back into the patient 12.

The dialysis fluid circulation comprises a dialysis liquid pump 9, a balancing equipment 10 and an ultrafiltration pump 11. With the dialysis liquid pump 9, the dialysis fluid is conveyed in counter-current to the blood through the dialyzer 3. The balancing equipment 10 serves for balancing the dialysis fluid of the dialysis fluid circulation, so that water is not extracted from the patient 12 in uncontrolled manner (dehydration) or he/she is not supplied with too much water (overhydration).

The dialyzer 3 usually consists substantially of numerous hollow fibers each comprising a semipermeable membrane. In the example which is explained on the basis of FIG. 1 (hemodialysis), blood is on one side of the membrane, namely on the side of the extracorporeal blood circulation (ECB), and an electrolyte solution, the so-called dialysis fluid, is on the other side, i.e. on the side of the dialysis fluid circulation (DKL). A diffusion and convection takes place via the membrane of the dialyzer 3, so that the blood is cleaned.

The exemplary embodiment according to FIG. 1 may further comprise additional measuring means, pumps, bubble catching devices etc. which are not shown.

Pressure transducers or pressure sensors 4, 5, 6 serve for monitoring the therapy processes. Specifically, these are an input pressure transducer 4 in the area of the air trap 2, an arterial pressure transducer 5 between the arterial cannula A and the arterial blood pump 1 as well as a venous pressure transducer 6 in the area of the venous air trap 7. In the following, the venous pressure sensor 6 is looked at in detail by way of example.

The venous pressure transducer 6 measures the pressure PV between the air trap 7 or the dialyzer 3 and the venous access V of the patient. Normally, PV is composed of the pressure generated by the blood pump 1 and the pressure in the venous access V of the patient. If there is a malfunction in the extracorporeal blood circulation in the form of a venous needle disconnection (VND), there will be a pressure drop at the venous access V, resulting in PV (venous pressure) showing a pressure drop which is detected with the pressure transducer 6. Due to the fact that the pressure drop corresponds to a VND, PV is a possible sensor value which can be used to detect an FEB in the context of the present invention.

For monitoring the dialysis machine, at least three components are employed according to aspects of the invention: at least two evaluation units each determining an evaluation criterion for identifying an FEB, at least two monitoring units each determining an FEB from the determined evaluation criteria of the evaluation unit, and a combination unit which combines, according to aspects of the invention, the monitoring units and hence the evaluation units. One, more or all three units mentioned above may each comprise a memory unit, an arithmetic unit, an energy supply means and a data line.

An evaluation criterion for identifying an FEB is determined by an evaluation unit for a specific state parameter which is detected with a suitable sensor prior to, during or after a therapy. Examples for evaluation units will be explained below. The evaluation units for the evaluation of the sensor values in the extracorporeal blood circulation can be chosen as desired and depend on the type of the sensor values. The evaluation units may be implemented as self-contained units or as logical units comprising the respective monitoring unit.

FIG. 2 shows a schematic illustration of a state machine for a system according to aspects of the invention. FIG. 3 gives an overview of the individual components and their connection to the dialysis machine.

The state machine provided for a system according to aspects of the invention and illustrated in FIG. 2 shows exemplary states which are passed for a singular/not yet combined identification of an FEB with a detected state parameter (sensor value) and an evaluation criterion applied thereon. In an initialization state, state parameters are initialized which have been evaluated with an arbitrary evaluation unit. To give an example, the evaluation unit may define the limits of a venous pressure PV as the evaluation criteria.

According to one embodiment, the system may stay in the initialization state or the initialization state may be maintained until a desired starting time of the evaluation unit is reached. The initialization advantageously starts at the beginning of a therapy. On the other hand, a re-initialization advantageously occurs after a disturbance variable has been identified and/or after an alarm has been triggered. In this context, disturbance variables may represent factors which could have an adverse effect on an evaluation criterion, so that an FEB is not recognized or is recognized in a wrong way (false alarm).

When the starting time is reached, the evaluation unit changes to an evaluation state in one embodiment of the invention. In said evaluation state, the evaluation unit is supplied with a sensor value as an input and, as the case may be, additionally with a possible disturbance variable with any scanning rate. If the disturbance variable changes, the corresponding evaluation criterion and the evaluation unit can be re-initialized. The re-initialization may be achieved by switching to the initialization state again.

In the evaluation state, an evaluation criterion for the state parameters detected with the sensor is defined preferably in continual manner. This is utilized to identify an FEB. If there are state parameters (e.g. PV values), for example, which are below a limit which is defined as an evaluation criterion, an FEB is assumed in the detection state.

According to an option of the invention, a period of time, in the following referred to as an identification period TIME, can be defined for identifying an FEB. If the state parameter measured by a sensor is outside defined evaluation criteria (limits) for a time which is longer than a selected identification period, an FEB is implied and is detected as such.

An identification period TIME, which has to be exceeded for the identification of an FEB, may be advantageously used to avoid false alarms which may be caused, for instance, by short-term state parameter deviations, e.g. pressure variations. Typically, the identification period TIME is determined depending on the characteristics of an evaluation unit and is not set on the basis of changes in sensor values, as it is known from the patent EP 1 815 878 B1, for example. If a sensor value is beyond the evaluation limits for a time which is not longer than the identification period TIME, a corresponding counter in the arithmetic unit of the monitoring unit concerned can be reset, so that the evaluation unit calculates a new evaluation criterion on the basis of the sensor values. If, however, the identification period TIME is exceeded for an evaluation criterion, there will be a change to the alerting state. In this state, an alarm is triggered. Preferably, possible consequences of an alarm are stopping the blood pump (actuator), closing the venous hose shut-off clip as well as alerting the patient and/or the nursing staff by acoustic and/or visual signals or the like. After a corresponding check and acknowledgement, there will be a change from the alerting state back to the initialization state again. In the latter state, the previously described procedure for identifying an FEB starts anew.

Sensor units, e.g. the pressure sensors 4, 5, 6, are in operative connection with the extracorporeal blood circulation ECB of the dialysis machine illustrated in FIG. 1. FIG. 3 shows the use of n sensor units, for example a first sensor unit 1 and an n-th sensor unit n, with n being a whole natural number. If there are e.g. three sensor units, n is equal to 3, in the case of five units n is equal to 5 etc.

Each sensor unit is connected to an evaluation unit 18, 19, 20 and forwards detected state parameters/sensor values to these. In the example of FIG. 3, the first sensor unit, e.g. the pressure transducer 4, is connected to a first evaluation unit 18 and then to a first monitoring unit 13, the second sensor unit, e.g. the pressure transducer 5, is connected to a second evaluation unit 19 and then to a second monitoring unit 14, and the n-th sensor unit, e.g. the pressure transducer 6, is connected to an n-th evaluation unit 20 and then to an n-th monitoring unit 15. Each evaluation unit 18, 19, 20 and each monitoring unit 13, 14, 15 comprises a memory unit and an arithmetic unit.

Finally, the monitoring units 1 to n (13, 14, 15) are connected to a combination unit 16 where the signals transmitted by the monitoring units 13, 14, 15 are processed (combined) and linked to result in a combined signal. The output of the combination unit 16 is used for controlling the dialysis machine in an open or closed loop, being indicated by a signal line 17.

According to the illustration of FIG. 3, each sensor unit 4, 5, 6 has an evaluation unit 18, 19, 20 associated to it.

After having been transmitted via data lines, the results of the individual monitoring units are combined in the combination unit. For combination, also this unit may utilize the corresponding state machine described above as well as an arithmetic unit, a memory unit, data lines and an energy supply means for identifying a VND/an FEB. In the example given here, the combination unit 16 controls corresponding actuators, among others a venous hose shut-off clip 8 and the blood pump 1 in the extracorporeal blood circulation via the data line 17, so that a safe state is assured in case a malfunction is detected in the extracorporeal blood circulation.

FIG. 3 illustrates the combination of several evaluation units 18, 19, 20 and monitoring units 13, 14, 15 with a combination unit 16. The monitoring units 13, 14, 15 monitor any sensor values independently of one another for a respective singular identification of an FEB. In this context, it is possible to use any evaluation units 18, 19, 20 of different or identical type, and also equal or different sensor values.

Figure 4:
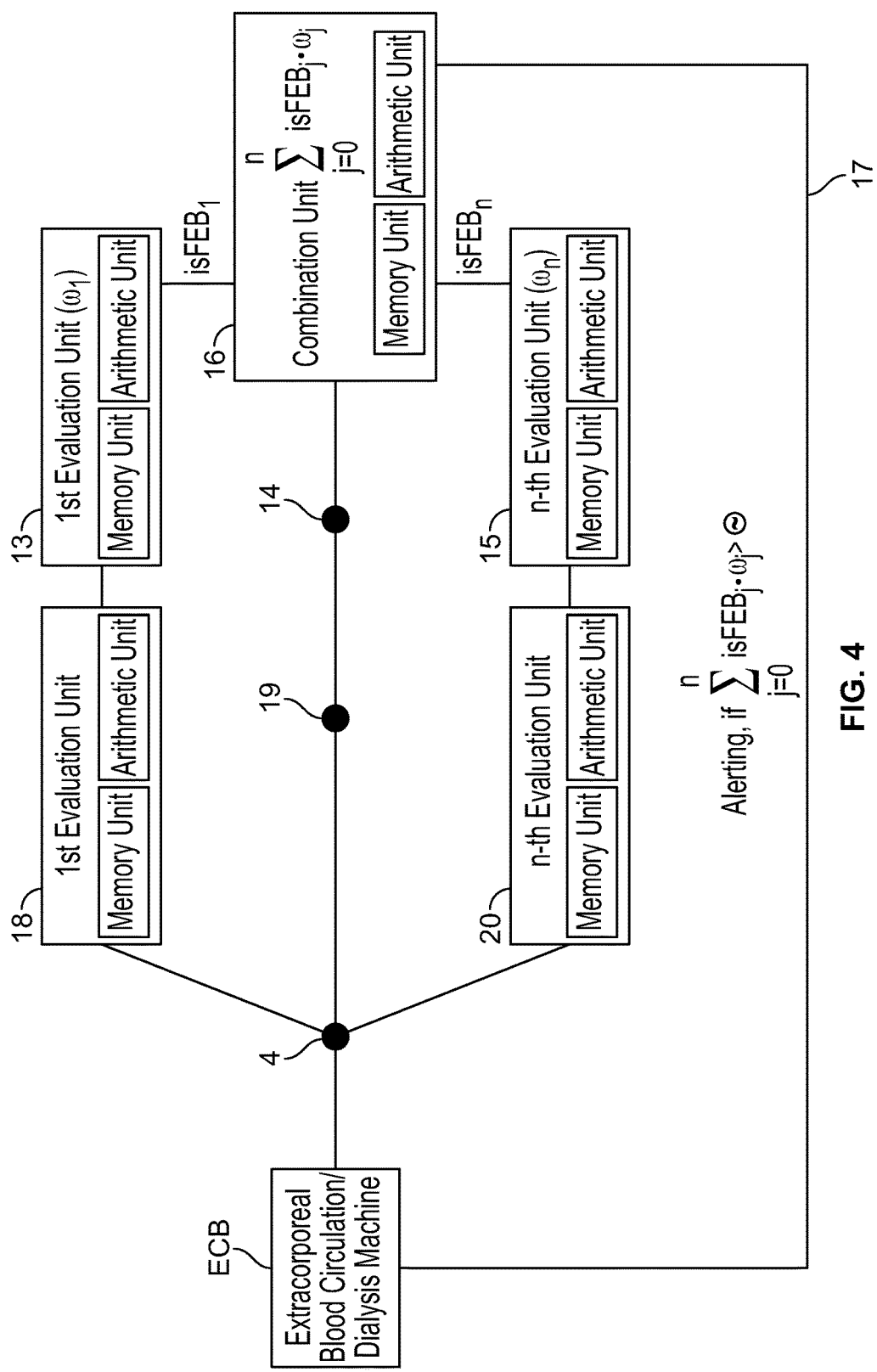
FIG. 4 is a schematic illustration of a second embodiment of the system according to aspects of the invention.

Corresponding to FIG. 4, one sensor unit 4 may also have several evaluation units 18, 19 and/or monitoring units 13, 14 associated to it. This means that state parameters (sensor values) detected with a sensor unit can be processed according to aspects of the invention not only by one evaluation unit and the monitoring unit associated to it, but the state parameters (sensor values) can also be delivered to several evaluation units where they are individually processed depending on the evaluation unit and forwarded to the corresponding monitoring unit.

At each point in time of the therapy, each monitoring unit has a variable isFEB as an output of the identification of malfunctions in the extracorporeal blood circulation. The variables isFEB are numbered in FIG. 3 in correspondence with the respective monitoring unit and are named $isFEB_1$ (for the first monitoring unit 13), $isFEB_2$ (for the second monitoring unit 14) and $isFEB_n$ (for the n-th monitoring unit 15). The variable isFEB is 1 in the case of an identified malfunction and is 0 in the event that no FEB has been identified. Here, reference is made to the fact that the variable may also take a value between 0 and 1. A combination of the individual monitoring units—which make use of various evaluation units for identifying an FEB—takes place in the combination unit 16. The variable isFEB of each of the monitoring units may be multiplied with a weighting w which is defined for each monitoring unit. The product of each multiplication for all monitoring units can be summed up in the arithmetic unit. In other words, the weighted sum of the outputs isFEB of the monitoring units can be established with the weighting w. If said sum exceeds a limit value θ, one can assume the presence of an FEB and an alert can be initiated.

The combination described above represents only one of numerous possible variants. It is within the scope of the invention to combine the monitoring units with all reasonable mathematical methods and models. Possible other combination variants, for instance, belong to the field of machine learning, for instance weighted or unweighted case analyses, fuzzy models, neuronal networks, SVRs or physical or mathematical models which depend on the temperature or any other physical variables.

The provision of several individual monitoring units and their combination with the combination unit allow that individual evaluation units can have an arbitrarily weighted proportion in the identification of an FEB. This is achieved by a suitable selection of the weighting w and of the limit value θ. Furthermore, a suitable selection of the respective starting time of the individual evaluation units allows to specify a starting order in which the following monitoring units begin to monitor state parameters. In addition, a suitable starting time further allows to define a temporal delay of the starting points of the evaluation units. These attributes allow the evaluation units to calculate their evaluation criteria (initially) on the basis of sensor values at different points in time and hence to represent a staggered alarm system. Advantageously, this circumstance can reduce or even minimize the number or occurrence frequency of false alarms.

Figure 5:
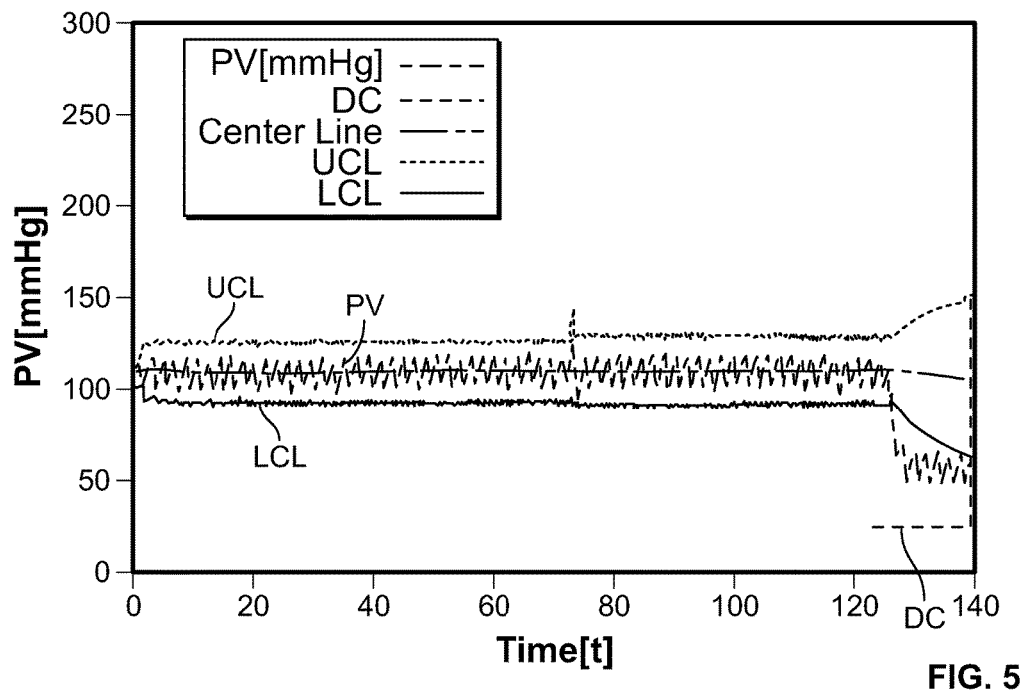
FIG. 5 shows a diagram illustrating the venous pressure curve of a patient along with upper and lower limits, which have been determined with a first evaluation unit, as evaluation criteria.
Figure 6:
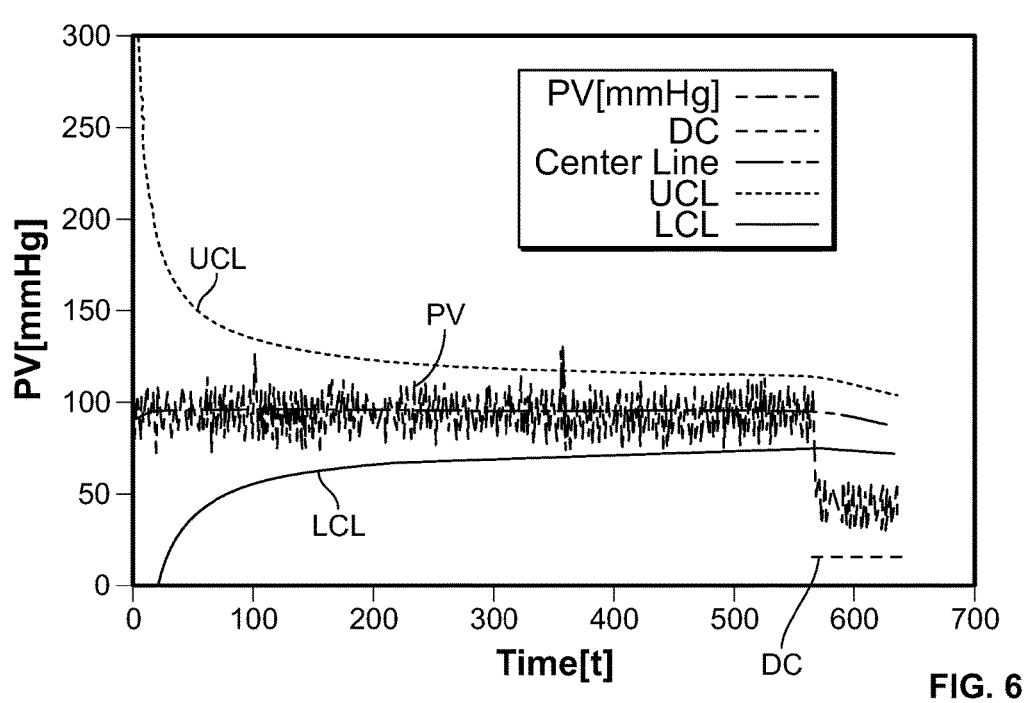
FIG. 6 shows a diagram illustrating the venous pressure curve of a patient along with upper and lower limits, which have been determined with a second evaluation unit, as evaluation criteria.

In the example of FIGS. 5 and 6, a first evaluation unit calculates a first evaluation criterion for identifying an FEB on the basis of the venous pressure PV, as a first state parameter, detected with the venous pressure transducer 6. Among others, this process results from FIG. 5 where the abscissa shows the time t in seconds and the ordinate shows the venous pressure PV in mmHG. A continuous line illustrates the course of the venous pressure PV. The first evaluation unit calculates evaluation criteria in the form of an upper limit (UCL, broken line) and a lower limit (LCL, dot-and-dash line) for the venous pressure. FIG. 5 and the way of calculation will be elucidated in more detail below.

A second evaluation unit calculates a second evaluation criterion on the basis of a state parameter, in the present example again captured by the venous pressure transducer 6 on the basis of the venous pressure PV. This procedure is apparent inter alia from FIG. 6 where the abscissa shows the time t in seconds and the ordinate shows the venous pressure PV in mmHG. A continuous line illustrates the course of the venous pressure PV. The second evaluation unit calculates a (second) upper limit (UCL, broken line) and a (second) lower limit (LCL, dot-and-dash line) for the venous pressure. FIG. 6 and the way of calculation will be elucidated in more detail below.

It is possible to use further evaluation units which calculate further evaluation criteria for the presence of an FEB for the same or different state parameters and with identical, similar or other calculation methods. In this respect, reference is made to FIG. 3.

According to aspects of the invention, a monitoring unit detects an FEB on the basis of an evaluation criterion calculated with an evaluation unit. With regard to the example of FIGS. 5 and 6, this means that a first monitoring unit, e.g. the monitoring unit 13, establishes the presence of an FEB on the basis of the first evaluation criterion (PV is between the first lower limit and the first upper limit) calculated by the first evaluation unit 18. To give an example, the first monitoring unit recognizes PV values outside the limit illustrated in FIG. 5, which are present for a longer time period, as being a venous needle disconnection. A second monitoring unit, e.g. the monitoring unit 14, establishes the presence of an FEB on the basis of the second evaluation criterion (PV is between the second lower limit and the second upper limit) calculated by the second evaluation unit 19. To give an example, the second monitoring unit recognizes PV values outside the limit illustrated in FIG. 6, which are present for a longer time period, as being a venous needle disconnection. A further monitoring unit or further monitoring units may establish the presence of an FEB on the basis of evaluation criteria calculated by one or more further evaluation units.

Each monitoring unit generates an error signal which is delivered to the combination unit 16. The latter is used for combining as many monitoring units as desired and hence also the error signals output by them. This combination is of decisive advantage. The presence of an FEB is implied not only on the basis of an evaluated error signal, as is known from prior art, but the combination unit processes a plurality of error signals which have been evaluated preferably in different ways. The strengths and weaknesses of the respective evaluation units and the evaluations processed therein are known, and in this way it is possible to improve the quality of detecting and displaying the malfunction and to minimize false alarms by a targeted selection or processing of the error signals delivered to the combination unit.

In the example of FIGS. 5 and 6, the venous pressure PV detected by the venous pressure transducer 6 is the state parameter which is under evaluation. The first evaluation unit 18 determines the above-mentioned evaluation criteria in the form of the upper limit (UCL) and lower limit (LCL) of the venous pressure on the basis of a polynomial regression, as is explained in more detail below.

The equation for the employed polynomial regression is as follows:

$$y(t) = w_0 + w_1 \cdot t + w_2 \cdot t^2 + \ldots + w_M \cdot t^M = \sum_{j=0}^{M} w_j \cdot t^j$$

In this equation, w is the weighting of a monom, t is the index of the therapy time and M is the highest order of the polynomial. The detected state parameter (PV value of the venous pressure transducer 6 as the sensor) is modeled by a calculation according to this equation. Any appearing deviation, the so-called approximation error, between the model of the sensor value and the actual sensor values is used for determining the evaluation criteria in the form of the lower limit (LCL for lower control limit) as well as the upper limit (UCL for upper control limit) with the aid of the following equations:

$$UCL_t := y(t) + k \cdot \sqrt{\frac{\sigma^2}{t}}$$

$$CenterPoint_t := y(t)$$

$$LCL_t := y(t) - k \cdot \sqrt{\frac{\sigma^2}{t}}$$

Here, k is a factor defining the width of the limit value window. The index of the therapy time t is used for determining the averaged approximation error of $\sigma^2$ at a certain point in time of the therapy. Then, the square root of said averaged error is calculated to determine the deviation at a desired index t. This deviation multiplied by the factor k plus or minus the modeled sensor value results in the upper limit of the venous pressure (UCL=upper control limit) and the lower limit of the venous pressure (LCL=lower control limit), respectively.

FIG. 5 illustrates the evaluation criteria which have been determined with the evaluation unit described above in the form of a polynomial regression. On the basis of the detected venous pressure PV and with the polynomial regression, the evaluation criteria in the form of the limits LCL and UCL are calculated over a period of 140 seconds. After approximately 125 seconds—said point in time is marked with DC (for disconnected)—a venous needle disconnection (VND) occurs in the illustrated example.

In FIG. 5, the "Center Line" CL represents a modeling of the venous pressure PV with a polynomial regression of order one. For calculating the limits UCL and LCL, a value of k=4 has been chosen. At the beginning of the calculation, the values have been set near the pulsation of PV. At the point in time DC of the venous needle disconnection, the limits will open. The variable TIME in the monitoring unit has to be chosen such that VND is realized early enough, in particular before the limits are opened too wide. In this example, only the lower limit LCL for identifying the VND is necessary, as the limit of a corresponding monitoring unit is used to identify a VND for PV values below LCL. However, for other sensor values or other malfunctions in the extracorporeal blood circulation, this upper limit UCL may also play a role for identifying.

Some advantages and disadvantages of the polynomial regression are apparent from FIG. 5. After a time lapse of approximately 75 seconds, one can see a short-term increase of the venous pressure in the form of a pulse peak. This entails, directly or within a very short time, a divergence of the upper and lower limits. Such a quick reaction to a short-term, unproblematic pulse peak is disadvantageous because of the divergence of the evaluation criteria. The phenomenon can also be seen after the occurrence of the disconnection DC. However, it is of advantage that—after the beginning of the measurement—the evaluation criteria in the form of the upper and lower limits are determined in a very short time (after approximately 2 to 3 seconds), and monitoring with respect to FEB is possible.

In the second evaluation unit (see FIG. 6), the evaluation criteria in the form of the upper limit (UCL) and the lower limit (LCL) of the venous pressure are determined on the basis of an "averaged exponential weighted average", as explained in more detail below.

The second evaluation unit is essentially based on an exponentially weighted average and a "heuristic" variance for determining the evaluation criteria in the form of the limits UCL and LCL. In the following, this evaluation unit is also referred to as EWMA. First, the weighting $\lambda_I$ with which a sensor value, here the venous pressure, is adopted in the mean, is determined with the equation:

$$\lambda_I = (1-\tilde{\lambda}) \cdot \lambda_{I-1} + \tilde{\lambda} \cdot \lambda_\infty$$

This is a recursive formula and the parameter $\tilde{\lambda}$ determines the decrease of the weighting for each recursive step. $\lambda_\infty$ an asymptotic value of the weighting, to which the weighting $\lambda_I$ converges. The equation $$Z_i := (1-\lambda_I) \cdot Z_{i-1} + \lambda_I \cdot X_I$$

specifies the actual exponentially weighted average. This equation is a recursive equation and also uses the sensor value X apart from the weighting, in order to calculate an average value. The result of a calculation with this equation is averaged once again using the following calculation:

$$p_t := \frac{1}{t} \cdot \sum_{i=1}^{t} Z_i,$$

$$\text{für } t \geq 1$$

In this way, it is reached in an advantageous way that the determination is more robust in terms of short-term fluctuations of the sensor value. The averaged result $p_I$ is used in the calculation of the variance according to the following equation $$V[p_t] = \frac{p_t(1-p_t)}{t} \cdot \left(1 - \frac{1}{t} \cdot \frac{1-\lambda_t}{\lambda_t(2-\lambda_t)} \cdot (1 - (1-\lambda_t)^t) \cdot (2 + (1-\lambda_t) \cdot (1 - (1-\lambda_t)^t))\right)$$

with the current weighting $\lambda_I$ to calculate the variance $V[p_I]$. The result of the variance $V[p_I]$ defines, along with the factor k and the value p, the evaluation criteria in the form of the upper limit UCL and the lower limit LCL at each point in time according to the following equations:

$$UCL_I := p_I + k \cdot \sqrt{V[p_I]}$$

$$CenterPoint_I := p_I$$

$$LCL_I := p_I - k \cdot \sqrt{V[p_I]}$$

FIG. 6 illustrates the evaluation criteria which are determined with the above-mentioned calculation. Sensor values PV of the venous pressure transducer have been detected as state parameters over a time period of 650 seconds. After a period of approximately 570 seconds, there is a venous needle disconnection (VND), and said point in time is marked as DC (disconnected).

The "Center Line" has been calculated by p. Further, factors k=3, $\lambda_\infty$=0.0095 and $\tilde{\lambda}$=0.01 have been used for the calculation. The first value of the weighting $\lambda_I$ has been initialized with 1.

FIG. 6 illustrates that the evaluation criteria, in the form of the upper limit UCL and lower limit LCL, which are determined according to the preceding calculation approach PV. However, this procedure takes a certain time, which is disadvantageous when using the second evaluation unit for identifying an FEB shortly after the beginning of the monitoring process, in the present case approximately within the first 300 seconds. But when the evaluation criteria in the form of the upper limit UCL and lower limit LCL are sufficiently close to the pulsation PV after the expiration of said time, they are robust against changes, as can be seen at point in time DC of the VND. Here too, only LCL is necessary for identifying a VND, but also UCL may be relevant in the case of other sensor values or FEBs.

If it should happen that an FEB is determined on the basis of one or both of the previously mentioned evaluation criteria and an error signal is output, a combination in a combination unit is performed according to aspects of the invention. In the present example, a grid search algorithm has been used for determining the optimum parameters for the combination unit. This is an optimization method which has been applied to a test data set of therapies with FEB and without FEB. In this way, it was possible to define most suitable parameters and possibly the best combinations of monitoring units. In doing so, various parameters and combinations are tested with grid search. Such parameters and combinations with the least number of false alarms and the highest number of detected FEBs are taken as the best possible combination or best possible parameters for identifying an FEB. For the optimization with grid search, e.g. five therapies with a respective duration of approximately four hours have been used. Here, ten venous needle disconnections have been simulated in each case. In the course of each individual therapy, machine parameters have been changed every 15 minutes in order to simulate therapy situations which are as difficult as possible and, usually or frequently, trigger false alarms. In order to ensure realistic data, the venous pressure curve during the simulated VNDs has been recorded under realistic conditions and with an internal shunt pressure and shunt flow as in a human.

In the preceding optimization on the basis of the data sets described above, three monitoring units as the best possible combination have been determined by grid search. Here, two polynomial regressions and one EWMA have been used as evaluation criterion. In doing so, the monitoring units are started with special advantage in the following order with a temporal offset of approximately 60 seconds:

1. polynomial regression
2. polynomial regression
3. EWMA

For each monitoring unit, the value for the weightings co amounted to 1.5 and the limit θ for identifying an FEB was 1.5. Each monitoring unit was able to recognize a VND independently of the other monitoring units. In the course of the determination with a polynomial regression, the values of the venous pressure PV had to be below the lower limit LCL for a period of approximately twelve seconds (TIME) for identifying a VND. With the EWMA method, the values of the venous pressure PV had to be below the lower limit LCL for a period of approximately 60 seconds. The other parameters were as described above and are summarized in the following table:

|  | M | K | Time [s] | $\lambda_\infty$ | $\tilde{\lambda}$ | Position | w | θ | Lag [s] |
|---|---|---|---|---|---|---|---|---|---|
| Polynomial regression | 1 | 4 | 12 | NA | NA | 1 | 1.5 | NA | NA |
| Polynomial regression | 1 | 4 | 12 | NA | NA | 2 | 1.5 | NA | NA |
| EWMA | NA | 3 | 60 | 0.095 | 0.01 | 3 | 1.5 | NA | NA |

This combination has been evaluated with the cited parameters for 58 VNDs, as an example of an FEB and on the basis of fifteen therapies without FEB with a respective duration of four hours. The data sets have been produced in exactly the same way as the data sets which have been used in the previously described grid search method, so that realistic conditions were ensured. The combination unit, with the combination described above and the parameters described above, has identified 55 of a total of 58 VNDs and has triggered 71 false alarms. Compared to this, a conventional alarm system has identified only one single VND and triggered 77 false alarms under identical conditions. This shows the potential of the invention presented here.

The invention claimed is:

1. A machine control method for identifying a malfunction in an extracorporeal blood circulation of an extracorporeal blood treatment machine, comprising:
    flowing blood of a patient through the extracorporeal blood circulation;
    initializing, with a first evaluation unit, at least one state parameter characterizing the extracorporeal blood circulation;
    detecting, with at least one sensor unit, the at least one state parameter characterizing the extracorporeal blood circulation;
    detecting, with the at least one sensor unit, at least one disturbance variable in the extracorporeal blood circulation;
    calculating, with the first evaluation unit, a first state parameter evaluation criterion for identifying at least one malfunction in the extracorporeal blood circulation using the at least one state parameter detected by the at least one sensor unit after initializing;
    monitoring, with a first monitoring unit connected with the first evaluation unit, the detected at least one state parameter;
    generating, with the first monitoring unit, a first error signal by using the first state parameter evaluation criterion, and making a decision with respect to the presence of at least one malfunction in the extracorporeal blood circulation;
    calculating, with a second evaluation unit, at least one second state parameter evaluation criterion using the at least one state parameter detected by the at least one sensor unit after initializing, the at least one second state parameter evaluation criterion different from the first state parameter evaluation criterion;
    monitoring, with a second monitoring unit connected with the second evaluation unit, the detected at least one state parameter;
    generating, with the second monitoring unit, a second error signal by using the at least one further evaluation criterion, and making a decision with respect to the presence of a malfunction in the extracorporeal blood circulation;
    combining, with a combination unit connected to the first monitoring unit and the second monitoring unit, the first error signal and the second error signal, and taking into consideration the at least one detected disturbance variable, to result in a combined error signal indicating the presence of a malfunction;
    triggering, with the combination unit, an alarm if the combined error signal exceeds a predetermined limit value in positive or negative direction or is within a predetermined value range; and
    re-initializing, with at least one of the first evaluation unit or the second evaluation unit, one or more state parameters characterizing the extracorporeal blood circulation and one or more state parameter evaluation criteria after triggering the alarm or after detecting the at least one disturbance variable, wherein the at least one detected disturbance variable is considered by the at least one of the first evaluation unit or the second evaluation unit during the re-initializing to adjust monitoring of the detected at least one state parameter.

2. The method according to claim 1, wherein at least one of the first or the second error signal is subjected to a weighting process.

3. The method according to claim 1, wherein the first error signal and the second error signal are combined by mathematically linking the error signals.

4. The method according to claim 1, wherein the at least one state parameter is initialized by assigning an initial value to the state parameter, and at least one of the first or the at least one second state parameter evaluation criterion is determined by using the initial value as well as state parameters detected after the initialization.

5. The method according to claim 1, wherein the detected at least one state parameter is monitored and the at least one malfunction is identified by means of the first state parameter evaluation criterion with a temporal offset relative to monitoring the detected at least one state parameter and identifying a malfunction by means of the at least a second state parameter evaluation criterion.

6. The method according to claim 1, wherein the at least one detected disturbance variable is an ultrafiltration rate, a dialysis fluid flow rate, a blood flow rate, a level control or a preceding alarm.

7. The method according to claim 1, wherein at least one of the first or the at least a second state parameter evaluation criterion is determined by means of a polynomial regression or by means of an exponentially weighted, moving average.

8. The method according to claim 1, wherein a monitored state parameter is the venous blood pressure or the arterial blood pressure.

9. A system for identifying a malfunction in an extracorporeal blood circulation of an extracorporeal blood treatment machine, using the machine control method according to claim 1, comprising:
the extracorporeal blood circulation through which blood of a patient is flowed;
at least one sensor configured to:
detect at least one state parameter characterizing the extracorporeal blood circulation, and
detect at least one disturbance variable in the extracorporeal blood circulation;
a first evaluation unit configured to:
initialize the at least one state parameter characterizing the extracorporeal blood circulation, and
calculate a first state parameter evaluation criterion for identifying the presence of the at least one malfunction in the extracorporeal blood circulation using the at least one state parameter detected by the at least one sensor after initializing;
a first monitoring unit connected with the first evaluation unit, the first monitoring unit configured to:
monitor the detected at least one state parameter,
generate a first error signal by using the first state parameter evaluation criterion, and
make a decision with respect to the presence of at least one malfunction in the extracorporeal blood circulation;
a second evaluation unit configured to calculate at least one second state parameter evaluation criterion using the at least one state parameter detected by the at least one sensor unit after initializing, the at least one second state parameter evaluation criterion different from the first state parameter evaluation criterion;
a second monitoring unit connected with the second evaluation unit, the second monitoring unit configured to:
monitor the detected at least one state parameter,
generate a second error signal by using the at least a second state parameter evaluation criterion, and
make a decision with respect to the presence of a malfunction in the extracorporeal blood circulation; and
a combination unit connected to the first monitoring unit and the second monitoring unit, the combination unit configured to:
combine the first error signal and the second error signal, and taking into consideration the at least one disturbance variable, to result in a combined error signal indicating the presence of a malfunction, and
trigger an alarm when the combined error signal exceeds a predetermined limit value in positive or negative direction or is within a predetermined value range; and wherein
at least one of the first evaluation unit or the second evaluation unit is further configured to re-initialize one or more state parameters characterizing the extracorporeal blood circulation and one or more state parameter evaluation criteria after triggering the alarm or after detecting the at least one disturbance variable, wherein the at least one detected disturbance variable is considered by the at least one of the first evaluation unit or the second evaluation unit during the re-initializing to adjust monitoring of the detected at least one state parameter.

10. The system according to claim 9, wherein each sensor is connected with only a single evaluation unit for determining a single state parameter evaluation criterion, and each sensor is associated with only a single monitoring unit.

11. The system according to claim 9, wherein each sensor is connected with a plurality of evaluation units for determining a plurality of state parameter evaluation criteria, and each sensor is associated with a plurality of monitoring units.

12. The system according to claim 9 wherein the system is part of the blood treatment machine.

13. The system according to claim 12, wherein the blood treatment machine is a dialysis machine.

14. The system according to claim 9, further comprising at least one of a display device or an alarm device for generating an indication or the alarm, respectively, if the combined error signal exceeds a predetermined limit value in positive or negative direction or is within a predetermined value range.

15. The system according to claim 9, further comprising an emergency stop switch for switching off the blood treatment machine if the combined error signal exceeds a predetermined limit value in positive or negative direction or is within a predetermined value range.

* * * * *